(12) United States Patent
Distler et al.

(10) Patent No.: US 7,381,808 B2
(45) Date of Patent: Jun. 3, 2008

(54) METHOD AND NUCLEIC ACIDS FOR THE DIFFERENTIATION OF PROSTATE TUMORS

(75) Inventors: Juergen Distler, Berlin (DE); Fabian Model, Berlin (DE); Peter Adorjan, Berlin (DE)

(73) Assignee: Epigenomics AG, Berlin (DE)

( * ) Notice: Subject to any disclaimer, the term of this patent is extended or adjusted under 35 U.S.C. 154(b) by 0 days.

(21) Appl. No.: 10/172,086

(22) Filed: Jun. 13, 2002

(65) Prior Publication Data
US 2003/0113750 A1 Jun. 19, 2003

(30) Foreign Application Priority Data
Jun. 14, 2001 (DE) .............................. 101 28 508

(51) Int. Cl.
C12Q 1/68 (2006.01)
C07H 21/04 (2006.01)
(52) U.S. Cl. ................... 536/23.1; 536/24.3; 435/91.1; 435/91.2
(58) Field of Classification Search ............... 536/23.1, 536/24.3; 435/6, 287.2
See application file for complete search history.

(56) References Cited

U.S. PATENT DOCUMENTS

| 5,474,796 A | * | 12/1995 | Brennan ................ 427/2.13 |
| 6,017,704 A | * | 1/2000 | Herman et al. ............ 435/6 |
| 2001/0053519 A1 | * | 12/2001 | Fodor et al. .............. 435/6 |
| 2003/0036081 A1 | | 2/2003 | Adorjan et al. |
| 2003/0143606 A1 | * | 7/2003 | Olek et al. ............... 435/6 |

FOREIGN PATENT DOCUMENTS

| CA | 2359182 | 8/2000 |
| DE | 1990508 | 1/1999 |
| WO | 0070090 | 5/2000 |
| WO | WO 01/68911 A1 | 9/2001 |
| WO | WO 01/68912 A1 | 9/2001 |
| WO | WO 01/76451 A1 | 10/2001 |
| WO | WO 01/77164 A1 | 10/2001 |
| WO | WO 01/77375 A1 | 10/2001 |
| WO | WO 01/77376 A1 | 10/2001 |
| WO | WO 01/77377 A1 | 10/2001 |
| WO | WO 01/81622 A1 | 11/2001 |
| WO | WO 01/92565 A1 | 12/2001 |
| WO | WO 02/00705 A1 | 1/2002 |
| WO | WO 02/00928 A1 | 1/2002 |
| WO | WO 02/02808 A1 | 1/2002 |
| WO | WO 02/20806 A3 | 3/2002 |
| WO | WO 02/12554 A1 | 2/2002 |
| WO | WO 02/36604 A1 | 5/2002 |
| WO | WO 02/36814 A1 | 5/2002 |
| WO | WO 02/02808 | * 1/2007 |
| WO | WO 0200705 | * 1/2007 |

OTHER PUBLICATIONS

Takahashi et al. "H. sapiens gene coding for ACTH and beta-LPH precursors." Genbank Accession No. V01510, Jun. 1997.*
Dynal Technical Handbook. 3rd Edition. 1998, p. 174.*
Mahairas et al. (Genbank Accession No. AQ178776, Oct. 1998).*
Dynal (Biomagnetic Techniques in Molecular Biology, 1998).*
Takahashi et al. (Genbank Accession V01510, Jun. 1997).*
NCI-CGAP (Genbank Accession AI341269, Feb. 1999).*
Jones, P.A., (Jun. 1, 1996) "DNA Methylation Errors and Cancer", Cancer Research, vol. 56 pp. 2463-2467.
Chan, M.F., et al. (2000), "Relationship Between Transcription and DNA Methylation", Curr Top Microbiol Immunol., vol. 249 pp. 75-86.
Huang, T.H.-M., et al., (1999) "Methylation profiling of CpG islands in human breast cancer cells" Human Molecular Genetics, vol. 8, No. 3 pp. 459-470, Oxford University Press.
Rein, T., et al., (1998) "Identifying 5-methylcytosine and related modifications in DNA genomes", Nucleic Acids Research, vol. 26, No. 10 pp. 2255-2264, Oxford University Press.
Santourlidis, S., et al., (1999) "High Frequency of Alterations in DNA Methylation in Adenocarcinoma of the Prostate", The Prostate, vol. 39 pp. 166-174, Wiley-Liss, Inc.
Florl, A.R., et al., (1999) "DNA methylation and expression of Line-1 and HERV-K provirus sequences in urothelial and renal cell carcinomas", British Journal of Cancer, vol. 80, No. 9 pp. 1312-1321, Cancer Research Campaign.
Olek, A., et al., (1996) "A modified and improved method for bisulphite based cytosine methylation analysis", Nucleic Acids Research, vol. 15, No. 24 pp. 5064-5066.
Zeschnigk, M., et al., (1997) "A single-tube PCR test for the diagnosis of Angelman and Prader-Willi syndrome based on allelic methylation differences at the SNPRN locus", Eur J Hum Genetics, vol. 5, No. 2 pp. 94-98.
Olek, A., et al., (1997) "The pre-implantation ontogeny of the H19 methylation imprint", Nature Genetics, vol. 17, No. 3 pp. 275-276.
Gonzalgo, ML., et al., (1997) "Rapid quantitation of methylation differences at specific sites using methylation-sensitive single nucleotide primer extension (Ms-SNuPE)", Nucleic Acid Research, vol. 25, No. 12 pp. 2529-2531.
Xiong, Z., et al., (1997) "COBRA: a sensitive and quantitative DNA methylation assay", Nucleic Acids Research, vol. 25, No. 12 pp. 2532-2534.
Grigg, G., et al., (1994) "Sequencing 5-methylcytosin residues in genomic DNA", Bioessays, vol. 16, No. 6 pp. 431-436.

(Continued)

*Primary Examiner*—Jeanine A. Goldberg
(74) *Attorney, Agent, or Firm*—Barry L. Davison; Davis Wright Tremaine LLP

(57) ABSTRACT

The present invention relates to chemically modified genomic sequences, to oligonucleotides and/or PNA-oligomers for detecting the cytosine methylation state of genomic DNA, as well as to a method for ascertaining genetic and/or epigenetic parameters of genes for use in characterisation, classification, differentiation, diagnosis and therapy of prostate lesions.

16 Claims, 1 Drawing Sheet
(1 of 1 Drawing Sheet(s) Filed in Color)

OTHER PUBLICATIONS

Zeschnigk, M., et al., (1997) "Imprinting segments in the human genome: different DNA methylation patterns in the Prader-Willi/Angelman syndrome region as determined by the genomic sequencing method", Human Molecular Genetics, vol. 6, No. 3 pp. 387-395.

Feil, R., et al., (1994) "Methylation analysis on individual chromosomes: improved protocol for bisulphite genomic sequencing", Nucleic Acids Research, vol. 22, No. 4 pp. 695-696.

Martin, V., et al., (1995) "Genomic sequencing indicates a correlation between DNA hypomethylaton in the 5' region of the pS2 gene and its expression in the human breast cancer cell lines", Gene, vol. 157, pp. 261-264.

Eckhardt et al., DNA methylation profiling of human chromosomes 6, 20 and 22, Nature Genet. 38:1378-1385, 2006.

* cited by examiner

METHOD AND NUCLEIC ACIDS FOR THE DIFFERENTIATION OF PROSTATE TUMORS

FIELD OF THE INVENTION

The levels of observation that have been studied by the methodological developments of recent years in molecular biology, are the genes themselves, the translation of these genes into RNA, and the resulting proteins. The question of which gene is switched on at which point in the course of the development of an individual, and how the activation and inhibition of specific genes in specific cells and tissues are controlled is correlatable to the degree and character of the methylation of the genes or of the genome. In this respect, pathogenic conditions may manifest themselves in a changed methylation pattern of individual genes or of the genome.

The present invention relates to nucleic acids, oligonucleotides, PNA-oligomers, and to a method for characterisation, classification, differentiation, and/or diagnosis of prostate lesions, or the predisposition to prostate cancer, by analysis of the genetic and/or epigenetic parameters of genomic DNA and, in particular, with the cytosine methylation status thereof.

PRIOR ART

Prostate cancer is a significant health care problem in Western countries with an incidence of 180 per 100 000 in the U.S. in 1999 (Cancer J Clin 1999;49:8). Different screening strategies are employed to improve early detection, including determination of levels of prostate specific antigen and digital rectal examination. If a prostate carcinoma is suspected in a patient, diagnosis of cancer is confirmed or excluded by the histological and cytological analysis of biopsy samples for features associated with malignant transformation. Particularly early stages of prostate carcinoma are often difficult to distinguish from benign hyperplasia of the prostate by routine histological examination even if an adequate biopsy is obtained (McNeal J E et al., Hum Pathol 2001, 32:441-6). Furthermore, small or otherwise insufficient biopsy samples sometimes impede routine analysis.

Molecular markers offer the advantage that even samples of very small sizes and samples whose tissue architecture has not been maintained can be analyzed quite efficiently. Within the last decade numerous genes have been shown to be differentially expressed between benign hyperplastic prostate tumors and different grades of prostate cancer. However, no single marker has been shown to be sufficient for the distinction between the two lesions so far. High-dimensional mRNA based approaches have recently been shown to be able to provide a better means to distinguish between different tumor types and benign and malignant lesions. Application as a routine diagnostic tool in a clinical environment is however impeded by the extreme instability of mRNA, the rapidly occurring expression changes following certain triggers (e.g. sample collection), and, most importantly, the large amount of mRNA needed for analysis (Lipshutz, R. J. et al., Nature Genetics 21:20-24, 1999; Bowtell, D. D. L. Nature genetics suppl. 21:25-32, 1999), which often cannot be obtained from a routine biopsy.

Aberrant DNA methylation within CpG islands is common in human malignancies leading to abrogation or overexpression of a broad spectrum of genes (Jones, P. A. Cancer Res 65:2463-2467, 1996). Abnormal methylation has also been shown to occur in CpG rich regulatory elements in intronic and coding parts of genes for certain tumours (Chan, M. F., et al., Curr Top Microbiol Immunol 249:75-86,2000). Highly characteristic DNA methylation patterns could also be shown for breast cancer cell lines (Huang, T. H.-M., et al., Hum Mol Genet 8:459-470, 1999).

5-methylcytosine is the most frequent covalent base modification in the DNA of eukaryotic cells. It plays a role, for example, in the regulation of the transcription, in genetic imprinting, and in tumorigenesis. Therefore, the identification of 5-methylcytosine as a component of genetic information is of considerable interest. However, 5-methylcytosine positions cannot be identified by sequencing since 5-methylcytosine has the same base pairing behavior as cytosine. Moreover, the epigenetic information carried by 5-methylcytosine is completely lost during PCR amplification.

A relatively new and currently the most frequently used method for analyzing DNA for 5-methylcytosine is based upon the specific reaction of bisulfite with cytosine which, upon subsequent alkaline hydrolysis, is converted to uracil which corresponds to thymidine in its base pairing behavior. However, 5-methylcytosine remains unmodified under these conditions. Consequently, the original DNA is converted in such a manner that methylcytosine, which originally could not be distinguished from cytosine by its hybridization behavior, can now be detected as the only remaining cytosine using "normal" molecular biological techniques, for example, by amplification and hybridization or sequencing. All of these techniques are based on base pairing which can now be fully exploited. In terms of sensitivity, the prior art is defined by a method which encloses the DNA to be analyzed in an agarose matrix, thus preventing the diffusion and renaturation of the DNA (bisulfite only reacts with single-stranded DNA), and which replaces all precipitation and purification steps with fast dialysis (Olek A, Oswald J, Walter J. A modified and improved method for bisulphite based cytosine methylation analysis. Nucleic Acids Res. Dec. 15, 1996; 24(24):5064-6, herein incorporated by reference). Using this method, it is possible to analyze individual cells, which illustrates the potential of the method. However, currently only individual regions of a length of up to approximately 3000 base pairs are analyzed, a global analysis of cells for thousands of possible methylation events is not possible. However, this method cannot reliably analyze very small fragments from small sample quantities either. These are lost through the matrix in spite of the diffusion protection.

An overview of the further known methods of detecting 5-methylcytosine may be gathered from the following review article: Rein, T., DePamphilis, M. L., Zorbas, H., Nucleic Acids Res. 1998, 26, 2255, herein incorporated by reference.

To date, barring few exceptions (e.g., Zeschnigk M, Lich C, Buiting K, Doerfler W, Horsthemke B. A single-tube PCR test for the diagnosis of Angelman and Prader-Willi syndrome based on allelic methylation differences at the SNRPN locus. Eur J Hum Genet. March-April 1997; 5(2): 94-8) the bisulfite technique is only used in research. Always, however, short, specific fragments of a known gene are amplified subsequent to a bisulfite treatment and either completely sequenced (Olek A, Walter J. The pre-implantation ontogeny of the H19 methylation imprint. Nat Genet. November 1997; 17(3):275-6) or individual cytosine positions are detected by a primer extension reaction (Gonzalgo M L, Jones P A. Rapid quantitation of methylation differences at specific sites using methylation-sensitive single nucleotide primer extension (Ms-SNuPE). Nucleic Acids Res. Jun. 15, 1997; 25(12):2529-31, WO 95/00669, herein incorporated by reference) or by enzymatic digestion (Xiong Z, Laird P W. COBRA: a sensitive and quantitative DNA methylation assay. Nucleic Acids Res. Jun. 15, 1997; 25(12): 2532-4, herein incorporated by reference). In addition, detection by hybridization has also been described (Olek et al., WO 99/28498, herein incorporated by reference).

Further publications dealing with the use of the bisulfite technique for methylation detection in individual genes are: Grigg G, Clark S. Sequencing 5-methylcytosine residues in genomic DNA. Bioessays. 1994 June;16(6):431-6, 431; Zeschnigk M, Schmitz B, Dittrich B, Buiting K, Horsthemke B, Doerfler W. Imprinted segments in the human genome: different DNA methylation patterns in the Prader-Willi/Angelman syndrome region as determined by the genomic sequencing method. Hum Mol Genet. March 1997; 6(3): 387-95; Feil R, Charlton J, Bird A P, Walter J, Reik W. Methylation analysis on individual chromosomes: improved protocol for bisulphite genomic sequencing. Nucleic Acids Res. Feb. 25, 1994; 22(4):695-6; Martin V, Ribieras S, Song-Wang X, Rio M C, Dante R. Genomic sequencing indicates a correlation between DNA hypomethylation in the 5' region of the pS2 gene and its expression in human breast cancer cell lines. Gene. May 19, 1995; 157(1-2):261-4; WO 97/46705, WO 95/15373 and WO 97/45560.

An overview of the Prior Art in oligomer array manufacturing can be gathered from a special edition of Nature Genetics (Nature Genetics Supplement, Volume 21, January 1999), published in January 1999, and from the literature cited therein.

Fluorescently labeled probes are often used for the scanning of immobilized DNA arrays. The simple attachment of Cy3 and Cy5 dyes to the 5'-OH of the specific probe are particularly suitable for fluorescence labels. The detection of the fluorescence of the hybridized probes may be carried out, for example via a confocal microscope. Cy3 and Cy5 dyes, besides many others, are commercially available.

Matrix Assisted Laser Desorption Ionization Mass Spectrometry (MALDI-TOF) is a very efficient development for the analysis of biomolecules (Karas M, Hillenkamp F. Laser desorption ionization of proteins with molecular masses exceeding 10,000 daltons. Anal Chem. Oct. 15, 1988; 60(20):2299-301). An analyte is embedded in a light-absorbing matrix. The matrix is evaporated by a short laser pulse thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones.

MALDI-TOF spectrometry is excellently suited to the analysis of peptides and proteins. The analysis of nucleic acids is somewhat more difficult (Gut I G, Beck S. DNA and Matrix Assisted Laser Desorption Ionization Mass Spectrometry. Current Innovations and Future Trends. 1995, 1; 147-57). The sensitivity to nucleic acids is approximately 100 times worse than to peptides and decreases disproportionally with increasing fragment size. For nucleic acids having a multiply negatively charged backbone, the ionization process via the matrix is considerably less efficient. In MALDI-TOF spectrometry, the selection of the matrix plays an eminently important role. For the desorption of peptides, several very efficient matrixes have been found which produce a very fine crystallization. There are now several responsive matrixes for DNA, however, the difference in sensitivity has not been reduced. The difference in sensitivity can be reduced by chemically modifying the DNA in such a manner that it becomes more similar to a peptide. Phosphorothioate nucleic acids in which the usual phosphates of the backbone are substituted with thiophosphates can be converted into a charge-neutral DNA using simple alkylation chemistry (Gut I G, Beck S. A procedure for selective DNA alkylation and detection by mass spectrometry. Nucleic Acids Res. Apr. 25, 1995; 23(8):1367-73). The coupling of a charge tag to this modified DNA results in an increase in sensitivity to the same level as that found for peptides. A further advantage of charge tagging is the increased stability of the analysis against impurities which make the detection of unmodified substrates considerably more difficult.

Genomic DNA is obtained from DNA of cell, tissue or other test samples using standard methods. This standard methodology is found in references such as Fritsch and Maniatis eds., Molecular Cloning: A Laboratory Manual, 1989.

DESCRIPTION

The disclosed invention provides a method and nucleic acids for the differentiation of prostate tumors. It discloses a means of distinguishing benign prostate hyperplasia from prostate carcinoma. This provides a means for the early detection and treatment of prostate cancer. Furthermore, the disclosed invention presents improvements over the state of the art in that current methods of prostate lesion differential diagnosis require the provision of a sample of sufficient size for histological and cytological examination. The method according to the present invention can be used for classification of minute samples.

The invention provides the chemically modified genomic DNA, as well as oligonucleotides and/or PNA-oligomers for detecting cytosine methylations, as well as a method which is particularly suitable for the classification, differentiation and/or diagnosis of prostate tumors, or the predisposition to prostate cancer. The present invention is based on the discovery that genetic and epigenetic parameters and, in particular, the cytosine methylation patterns of genomic DNA are particularly suitable for classification, differentiation and/or diagnosis of prostate tumors, in particular for use in differential diagnosis of prostate cancer.

This objective is achieved according to the present invention providing a nucleic acid containing a sequence of at least 18 bases in length of the chemically pretreated genomic DNA according to one of Seq. ID No.1 through Seq. ID No.112, and sequences complementary thereto.

The chemically modified nucleic acid could heretofore not be connected with the ascertainment of disease relevant genetic and epigenetic parameters.

The object of the present invention is further achieved by an oligonucleotide or oligomer for detecting the cytosine methylation state in chemically pretreated DNA, containing at least one base sequence having a length of at least 9 to 13 nucleotides which hybridizes to a chemically pretreated genomic DNA according to Seq. ID No.1 through Seq. ID No.112. The oligomer probes according to the present invention constitute important and effective tools which, for the first time, make it possible to ascertain specific genetic and epigenetic parameters of carcinomas, in particular, for use in differential diagnosis of prostate tumors and for diagnosis of predisposition to prostate carcinomas. The base sequence of the oligomers preferably contains at least one CpG dinucleotide. The probes may also exist in the form of a PNA (peptide nucleic acid) which has particularly preferred pairing properties. Particularly preferred are oligonucleotides according to the present invention in which the cytosine of the CpG dinucleotide is the $5^{th}$-$9^{th}$ nucleotide from the 5'-end of the 13-mer; in the case of PNA-oligomers, it is preferred for the cytosine of the CpG dinucleotide to be the $4^{th}$-$6^{th}$ nucleotide from the 5'-end of the 9-mer.

The oligomers according to the present invention are normally used in so called "sets" which contain at least one oligomer for each of the CpG dinucleotides of the sequences of Seq. ID No.1 through Seq. ID No.112. Preferred is a set which contains at least one oligomer for each of the CpG dinucleotides from one of Seq. ID No.1 through Seq. ID No.112.

Moreover, the present invention makes available a set of at least two oligonucleotides which can be used as so-called "primer oligonucleotides" for amplifying DNA sequences of one of Seq. ID No.1 through Seq. ID No.112, or segments thereof, for example using PCR.

In the case of the sets of oligonucleotides according to the present invention, it is preferred that at least one oligonucleotide is bound to a solid phase. It is further preferred that all the oligonucleotides of one set are bound to a solid phase.

The present invention moreover relates to a set of at least 10 n (oligonucleotides and/or PNA-oligomers) used for detecting the cytosine methylation state in chemically pretreated genomic DNA (Seq. ID No.1 through Seq. ID No.112). These probes enable classification, differentiation and/or diagnosis of genetic and epigenetic parameters of tumors, which are particularly useful in differential diagnosis of prostate cancer. Furthermore, the probes enable the diagnosis of predisposition to prostate cancer. The set of oligomers may also be used for detecting single nucleotide polymorphisms (SNPs) in chemically pretreated genomic DNA according to one of Seq. ID No.1 through Seq. ID No.112.

According to the present invention, it is preferred that an arrangement of different oligonucleotides and/or PNA-oligomers (a so-called "array") made available by the present invention is present in a manner that it is likewise bound to a solid phase. This array of different oligonucleotide- and/or PNA-oligomer sequences can be characterized in that it is arranged on the solid phase in the form of a rectangular or hexagonal lattice. The solid phase surface is preferably composed of silicon, glass, polystyrene, aluminum, steel, iron, copper, nickel, silver, or gold. However, nitrocellulose as well as plastics such as nylon which can exist in the form of pellets or also as resin matrices are possible as well.

Therefore, a further subject matter of the present invention is a method for manufacturing an array fixed to a carrier material for the classification, differentiation and/or diagnosis of prostate tumors, in particular, differential diagnosis of prostate cancer or for the classification, differentiation and/or diagnosis of prostate lesions or the predisposition to prostate carcinoma and/or for the therapy of prostate carcinoma, in which method at least one oligomer according to the present invention is coupled to a solid phase. Methods for manufacturing such arrays are known, for example, from U.S. Pat. No. 5,744,305 (herein incorporated by reference) by means of solid-phase chemistry and photolabile protecting groups.

A further subject matter of the present invention relates to a DNA chip for the classification, differentiation and/or diagnosis of prostate tumors, in particular, differential diagnosis of prostate cancer or for the classification, differentiation and/or diagnosis of prostate lesions or the predisposition to prostate carcinoma and/or for the therapy of prostate carcinoma. Furthermore the DNA chip enables the diagnosis of predisposition to prostate carcinomas. The DNA chip contains at least one nucleic acid according to the present invention. DNA chips are known, for example, for U.S. Pat. No. 5,837,832, incorporated herein by reference.

Moreover, a subject matter of the present invention is a kit which may be composed, for example, of a bisulfite-containing reagent, a set of primer oligonucleotides containing at least two oligonucleotides whose sequences in each case correspond or are complementary to an 18 base long segment of the base sequences specified in the appendix (Seq. ID No.1 through Seq. ID No.112), oligonucleotides and/or PNA-oligomers as well as instructions for carrying out and evaluating the described method. However, a kit along the lines of the present invention can also contain only part of the aforementioned components. Preferred is a kit, wherein the additional standard methylation assay reagents are standard reagents for performing a methylation assay from the group consisting of MS-SNuPE, COBRA, and combinations thereof.

The present invention also makes available a method for ascertaining genetic and/or epigenetic parameters of genomic DNA. The method is for use in the classification, differentiation and/or diagnosis of prostate tumors, in particular for the differential diagnosis of prostate cancer and diagnosis of predisposition to prostate cancer. The method enables the analysis of cytosine methylations and single nucleotide polymorphisms, including the following steps:

In the first step of the method the genomic DNA sample must be isolated (i.e. obtained) from tissue or cellular sources. Such sources may include cell lines, histological slides, body fluids, for example blood, sputum, faeces, urine, cerebrospinal fluid, lymphatic fluid tissue embedded in paraffin; for example, prostate or lymphatic tissue. Extraction may be by means that are standard to one skilled in the art, these include the use of detergent lysates, sonification and vortexing with glass beads. Once the nucleic acids have been extracted the genomic double stranded DNA is used in the analysis.

In a preferred embodiment the DNA may be cleaved prior to the chemical treatment, this may be any means standard in the state of the art, in particular with restriction endonucleases.

In the second step of the method, the genomic DNA sample is chemically treated in such a manner that cytosine bases which are unmethylated at the 5'-position are converted to uracil, thymine, or another base which is dissimilar to cytosine in terms of hybridization behavior. This will be herein understood as "chemical pretreatment".

The above described treatment of genomic DNA is preferably carried out with bisulfite (sulfite, disulfite) and subsequent alkaline hydrolysis which results in a conversion of non-methylated cytosine nucleobases to uracil or to another base which is dissimilar to cytosine in terms of base pairing behavior.

Fragments of the chemically pretreated DNA are amplified, using sets of primer oligonucleotides according to the present invention, and a, preferably heat-stable polymerase. Because of statistical and practical considerations, preferably more than ten different fragments having a length of 100-2000 base pairs are amplified. The amplification of several DNA segments can be carried out simultaneously in one and the same reaction vessel. Usually, the amplification is carried out by means of a polymerase chain reaction (PCR).

In a preferred embodiment of the method, the set of primer oligonucleotides includes at least two olignonucleotides whose sequences are each reverse complementary or identical to an at least 18 base-pair long segment of the base sequences specified in the appendix (Seq. ID No.1 through Seq. ID No.112). The primer oligonucleotides are preferably characterized in that they do not contain any CpG dinucleotides. In a particularly preferred embodiment of the method, the sequence of said primer oligonucleotides are designed so as to selectively anneal to and amplify, only the prostate specific DNA of interest, thereby minimizing the amplification of background or non relevant DNA, i.e. that the amplification step preferentially amplifies DNA which is of particularly interest in prostate cells, based on the specific genomic methylation status of prostate cells, as opposed to background DNA. In the context of the present invention, background DNA is taken to mean genomic DNA which does not have a relevant tissue specific methylation pattern, in this case the relevant tissue being prostate and prostate carcinoma tissue. Examples of such primers, used in Example 2, are contained in Table 1. The amplification of several DNA segments can be carried out in one reaction vessel using a polymerase is a heat-resistant DNA polymerase.

According to the present invention, it is preferred that at least one primer oligonucleotide is bonded to a solid phase during amplification. The different oligonucleotide and/or PNA-oligomer sequences can be arranged on a plane solid phase in the form of a rectangular or hexagonal lattice, the solid phase surface preferably being composed of silicon, glass, polystyrene, aluminium, steel, iron, copper, nickel, silver, or gold, it being possible for other materials such as nitrocellulose or plastics to be used as well.

In a next preferred step of the method, the methylation status of one or more cytosine positions is identified. This can be done in a number of ways that are generally known to the person skilled in the art. Some methods are described in more detail, below.

The fragments obtained by means of the amplification can carry a directly or indirectly detectable label. Preferred are labels in the form of fluorescence labels, radionuclides, or detachable molecule fragments having a typical mass which can be detected in a mass spectrometer, it being preferred that the fragments that are produced have a single positive or negative net charge for better detectability in the mass spectrometer. The detection may be carried out and visualized by means of matrix assisted laser desorption/ionization mass spectrometry (MALDI) or using electron spray mass spectrometry (ESI).

In a preferred embodiment, the amplificates obtained in the second step of the method are subsequently hybridized to an array or a set of oligonucleotides and/or PNA probes. In this context, the hybridization takes place in the manner described in the following. The set of probes used during the hybridization is preferably composed of at least 10 oligonucleotides or PNA-oligomers. In the process, the amplificates serve as probes which hybridize to oligonucleotides previously bonded to a solid phase. The non-hybridized fragments are subsequently removed. Said oligonucleotides contain at least one base sequence having a length of 13 nucleotides which is reverse complementary or identical to a segment of the base sequences specified in the appendix, the segment containing at least one CpG dinucleotide. The cytosine of the CpG dinucleotide is the $5^{th}$ to $9^{th}$ nucleotide from the 5'-end of the 13-mer. One oligonucleotide exists for each CpG dinucleotide. Said PNA-oligomers contain at least one base sequence having a length of 9 nucleotides which is reverse complementary or identical to a segment of the base sequences specified in the appendix, the segment containing at least one CpG dinucleotide. The cytosine of the CpG dinucleotide is the $4^{th}$ to $6^{th}$ nucleotide seen from the 5'-end of the 9-mer. Preferably one oligonucleotide exists for each CpG dinucleotide.

In the fifth step of the method, the non-hybridized amplificates are removed.

In the final step of the method, the hybridized amplificates are detected. In this context, it is preferred that labels attached to the amplificates are identifiable at each position of the solid phase at which an oligonucleotide sequence is located. In this final step, also an analysis of the methylation status of the cytosine positions by reference to one or more data sets can be present.

According to the present invention, it is preferred that the labels of the amplificates are fluorescence labels, radionuclides, or detachable molecule fragments having a typical mass which can be detected in a mass spectrometer. The mass spectrometer is preferred for the detection of the amplificates, fragments of the amplificates or of probes which are complementary to the amplificates, it being possible for the detection to be carried out and visualized by means of matrix assisted laser desorption/ionization mass spectrometry (MALDI) or using electron spray mass spectrometry (ESI). The produced fragments may have a single positive or negative net charge for better detectability in the mass spectrometer.

The aforementioned method is preferably used for ascertaining genetic and/or epigenetic parameters of genomic DNA.

The oligomers according to the present invention or arrays thereof as well as a kit according to the present invention are intended to be used for the classification, differentiation and/or diagnosis of prostate tumors. More preferably for the differential diagnosis of prostate tumors, or diagnosis of predisposition to prostate cancer. According to the present invention, the method is preferably used for classification, differentiation and/or diagnosis of important genetic and/or epigenetic parameters within genomic DNA, in particular for use in differential diagnosis of prostate tumors and predisposition to prostate cancer.

The method according to the present invention is used, for example, for classification, differentiation and/or diagnosis of prostate tumors.

The nucleic acids according to the present invention of Seq. ID No.1 through Seq. ID No.112 can be used for classification, differentiation and/or diagnosis of genetic and/or epigenetic parameters of genomic DNA, in particular for use in differential diagnosis of prostate tumors.

The present invention moreover relates to a method for manufacturing a diagnostic reagent and/or therapeutic agent for classification, differentiation and/or diagnosis of prostate tumours and cancer by analyzing methylation patterns of genomic DNA. More preferably for use in differential diagnosis of prostate tumors. The diagnostic reagent and/or therapeutic agent being characterized in that at least one nucleic acid according to the present invention (sequence IDs 1 through 112) is used for manufacturing it, preferably together with suitable additives and auxiliary agents.

A further subject matter of the present invention relates to a diagnostic reagent and/or therapeutic agent for prostate cancer by analyzing methylation patterns of genomic DNA, in particular for use in differential diagnosis of prostate tumors, or diagnosis of the predisposition to prostate cancer, the diagnostic reagent and/or therapeutic agent containing at least one nucleic acid according to the present invention (sequence IDs 1 through 112), preferably together with suitable additives and auxiliary agents.

The present invention moreover relates to the diagnosis and/or prognosis of events which are disadvantageous to patients or individuals in which important genetic and/or epigenetic parameters within genomic DNA, said parameters obtained by means of the present invention may be compared to another set of genetic and/or epigenetic parameters, the differences serving as the basis for a diagnosis and/or prognosis of events which are disadvantageous to patients or individuals.

In the context of the present invention the term "hybridization" is to be understood as a bond of an oligonucleotide to a completely complementary sequence along the lines of the Watson-Crick base pairings in the sample DNA, forming a duplex structure.

The term "functional variants" denotes all DNA sequences which are complementary to a DNA sequence, and which hybridize to the reference sequence under stringent conditions.

In the context of the present invention, "genetic parameters" are mutations and polymorphisms of genomic DNA and sequences further required for their regulation. To be designated as mutations are, in particular, insertions, deletions, point mutations, inversions and polymorphisms and, particularly preferred, SNPs (single nucleotide polymorphisms).

In the context of the present invention, "epigenetic parameters" are, in particular, cytosine methylations and further chemical modifications of DNA bases of genomic DNA and sequences further required for their regulation. Further epigenetic parameters include, for example, the acetylation of histones which, cannot be directly analyzed using the described method but which, in turn, correlates with the DNA methylation.

In the following, the present invention will be explained in greater detail on the basis of the sequences and examples with respect to the attached drawing without being limited thereto.

DESCRIPTION OF FIGURE

The patent or application file contains at least one drawing executed in color. Copies of this patent or patent application publication with color drawing(s) will be provided by the Office upon request and payment of the necessary fee.

FIG. 1 shows the separation of benign prostate hyperplasia (1) and prostate carcinoma (2). High probability of methylation corresponds to red, uncertainty to black and low probability to green. The labels on the left side of the plot are gene and CpG identifiers. The labels on the right side give the significance (p-value) of the difference between the means of the two groups. Each row corresponds to a single CpG and each column to the methylation levels of one sample. CpGs are ordered according to their contribution to the distinction to the differential diagnosis of the two lesions with increasing contribution from top to bottom.

Figure 1:
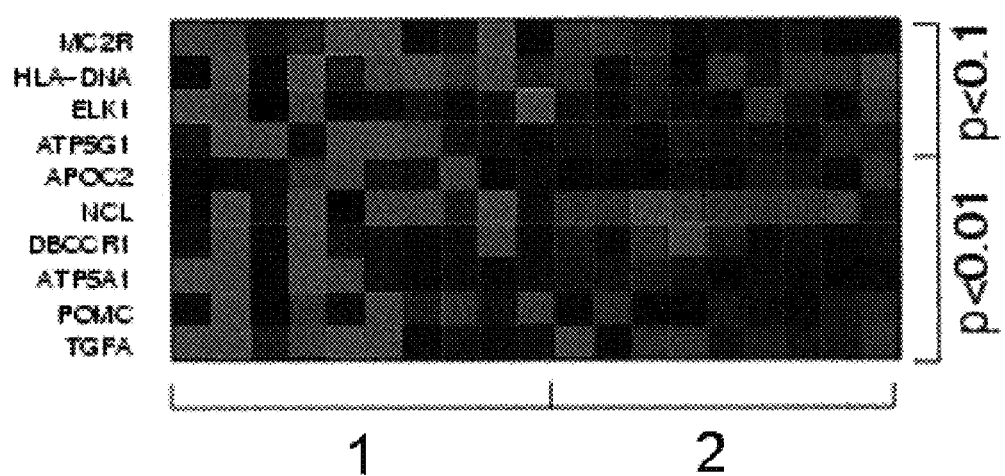
FIG. 1

Seq. ID No.1 trough Seq. ID No.112

Sequences having odd sequence numbers (e.g., Seq. ID No. 1, 3, 5, . . . ) exhibit in each case sequences of chemically pretreated genomic DNAs. Sequences having even sequence numbers (e.g., Seq. ID No. 2, 4, 6, . . . ) exhibit in each case the sequences of the chemically pretreated genomic DNAs which are complementary to the preceding sequences (e.g., the complementary sequence to Seq. ID No.1 is Seq. ID No.2, the complementary sequence to Seq. ID No.3 is Seq. ID No.4, etc.).

Seq. ID No.113 trough Seq. ID No.116

Seq. ID No.113 trough Seq. ID No.116 show sequences of oligonucleotides used in Example 1.

The following example relates to a fragment of a gene, in this case, TGF-alpha in which a specific CG-position is analyzed for its methylation status.

EXAMPLE 1

Methylation Analysis of the Gene TGF-alpha

The following example relates to a fragment of the gene TGF-alpha in which a specific CG-position is to be analyzed for methylation.

In the first step, a genomic sequence is treated using bisulfite (hydrogen sulfite, disulfite) in such a manner that all cytosines which are not methylated at the 5-position of the base are modified in such a manner that a different base is substituted with regard to the base pairing behavior while the cytosines methylated at the 5-position remain unchanged.

If bisulfite solution is used for the reaction, then an addition takes place at the non-methylated cytosine bases. Moreover, a denaturating reagent or solvent as well as a radical interceptor must be present. A subsequent alkaline hydrolysis then gives rise to the conversion of non-methylated cytosine nucleobases to uracil. The chemically converted DNA is then used for the detection of methylated cytosines. In the second method step, the treated DNA sample is diluted with water or an aqueous solution. Preferably, the DNA is subsequently desulfonated. In the third step of the method, the DNA sample is amplified in a polymerase chain reaction, preferably using a heat-resistant DNA polymerase. In the present case, cytosines of the gene TGF-alpha are analyzed. To this end, a defined fragment having a length of 531 bp is amplified with the specific primer oligonucleotides GGTTTGTTTGGGAGGTAAG (Sequence ID 113) and CCCCCTAAAAACACAAAA (Sequence ID No. 114). This amplificate serves as a sample which hybridizes to an oligonucleotide previously bound to a solid phase, forming a duplex structure, for example GTTTTTTTCGTTTTAGAG (Sequence ID No. 115), the cytosine to be detected being located at position 188 of the amplificate. The detection of the hybridization product is based on Cy3 and Cy5 fluorescently labelled primer oligonucleotides which have been used for the amplification. A hybridization reaction of the amplified DNA with the oligonucleotide takes place only if a methylated cytosine was present at this location in the bisulfite-treated DNA. Thus, the methylation status of the specific cytosine to be analyzed is inferred from the hybridization product.

In order to verify the methylation status of the position, a sample of the amplificate is further hybridized to another oligonucleotide previously bonded to a solid phase. Said olignonucleotide is identical to the oligonucleotide previously used to analyze the methylation status of the sample, with the exception of the position in question. At the position to be analysed said oligonucleotide comprises a thymine base as opposed to a cytosine base i.e GTTTTTTTTGTTTTAGAG (Sequence ID No. 116). Therefore, the hybridisation reaction only takes place if an unmethylated cytosine was present at the position to be analysed.

EXAMPLE 2

Differentiation of Prostate Tumors

In order to relate the methylation patterns to a specific tumour type, it is initially required to analyze the DNA methylation patterns of two groups of patients with alternative forms of a tumor, in this case one group of benign prostate hyperplasia and another group of prostate carcinoma. These analyses were carried out, analogously to Example 1. The results obtained in this manner are stored in a database and the CpG dinucleotides which are methylated differently between the two groups are identified. This can be carried out by determining individual CpG methylation rates as can be done, for example, by sequencing, which is a relatively imprecise method of quantifying methylation at a specific CpG, or else, in a very precise manner, by a methylation-sensitive "primer extension reaction". In a particularly preferred variant the methylation status of hundreds or thousands of CpGs may be analysed on an oligomer array. It is also possible for the patterns to be compared, for example, by clustering analyses which can be carried out, for example, by a computer.

All clinical specimens were obtained at time of surgery, i.e. in a routine clinical situation (Santourlidis, S., Prostate 39:166-174, 1999, Florl, A. R., Br. J. Cancer 80:1312-1321, 1999). A panel of genomic fragments from 56 different genes (listed in Table 1) were bisulphite treated according to Example 1 and amplified by PCR. The genomic DNA was amplified using the primer pairs listed in Table 1. However, as will be obvious to one skilled in the art, it is also possible to use other primers that amplify the genomic in an adequate manner, the design of such primers will be obvious to one skilled in the art. However the primer pairs as listed in Table 1 are particularly preferred. Optimal results were obtained by including at least 8 CpG dinucleotides, the most informative CpG positions for this discrimination being located within the TGF-alpha and POMC genes. Most other CpGs of the panel showed different methylation patterns between the two phenotypes, too. The results prove that methylation fingerprints are capable of providing differential diagnosis of solid malignant tumours and could therefore be applied in a large number clinical situations. FIG. 1 shows the application of the described method to distinguish benign prostate hyperplasia from prostate carcinoma.

TABLE 1

List of genes and primer oligonucleotides according to Example 2

| Name | Genbank Entry No. (internet address: ttp://www.ncbi.nlm.nih.gov) | Primer 1 | Primer 2 |
| --- | --- | --- | --- |
| ADCYAP1 | NM_001117 | GGTGGATTTATGGTTATTTTG | TCCCTCCCTTACCCTTCAAC |
| AFP | NM_001134 | AGGTTTATTGAATATTTAGG | AACATATTTCCACAACATCC |
| APOA1 | NM_000039 | GTTGGTGGTGGGGGAGGTAG | ACAACCAAAATCTAAACTAA |
| APOC2 | NM_000483 | ATGAGTAGAAGAGGTGATAT | CCCTAAATCCCTTTCTTACC |
| ATP5A1 | NM_004046 | AGTTTGTTTAATTTATTGATAGGA | AACAACATCTTTACAATTACTCC |
| ATP5G1 | NM_005175 | TGATAGTTTATGATTGTTGA | AATCTCAACCCTCAACTTCC |
| ATP6 | NC_001807 | GGGTATTAGGAATTTATGTG | CAAAACACCTTCCTAACTCA |
| C4B | NM_000592 | ATTGATAGGTAGTTAGATTGG | AAAAAACTCTCATAAATCTCA |
| c-abl | NM_007313 | GGTTGGGAGATTTAATTTATT | ACCAATCCAAACTTTTCCTT |
| CD1R3 | NM_001766 | ATTATGGTTGGAATTGTAAT | ACAAAAACAACAAACACCCC |
| CDC25A | NM_001789 | AGAAGTTGTTTATTGATTGG | AAAATTAAATCCAAACAAAC |
| CDH3 | NM_001793 | GTTTAGAAGTTTAAGATTAG | CAAAAACTCAACCTCTATCT |
| c-fos | NM_005252 | TTTTGAGTTTTAGAATTGTTTTTAG | AAAAACCCCCTACTCATCTACTA |

TABLE 1-continued

List of genes and primer oligonucleotides according to Example 2

| Name | Genbank Entry No. (internet address: ttp://www.ncbi.nlm.nih.gov) | Primer 1 | Primer 2 |
|---|---|---|---|
| c-MOS | NM_005372 | TTTATTGATTGGGAGTAGGT | CTAATTTTACAAACATCCTA |
| c-myc | NM_002467 | AAAGGTTTGGAGGTAGGAGT | TTCCTTTCCAAATCCTCTTT |
| CRIP1 | NM_001311 | TTTAGGTTTAGGGTTTAGTT | CCACTCCAAAACTAATATCA |
| CSF1 | NM_000757 | TAGGGTTTGGAGGGAAAG | AAAAATCACCCTAACCAAAC |
| CSNK2B | NM_001320 | GGGGAAATGGAGAAGTGTAA | CTACCAATCCCAAAATAACC |
| CTLA4 | NM_005214 | TTTTTATGGAGAGTAGTTGG | TAACTTTACTCACCAATTAC |
| DAD1 | NM_001344 | TTTTGTTGTTAGAGTAATTG | ACCTCAATTTCCCCATTCAC |
| DAPK1 | NM_004938 | ATTAATATTATGTAAAGTGA | CTTACAACCATTCACCCACA |
| DBCCR1 | NM_014618 | ATTTGGAGTTGAAGTATTTG | AACTATACCCAAACACCTAC |
| EGFR | NM_005228 | GGGTAGTGGGATATTTAGTTTTT | CCAACACTACCCCTCTAA |
| EGR4 | NM_001965 | AGGGGGATTGAGTGTTAAGT | CCCAAACATAAACACAAAAT |
| ELK1 | NM_005229 | AAGTGTTTTAGTTTTTAATGGGTA | CAAACCCAAAACTCACCTAT |
| ERBB2 | NM_004448 | GAGTGATATTTTTATTTTATGTTTGG | AAAACCCTAACTCAACTACTCAC |
| G6E | NM_024123 | AGGTTGGATTTTGGGTAGGT | TCTCCTACTCTCCTAATCTC |
| GP1BB | NM_000407 | GGTGATAGGAGAATAATGTTGG | TCTCCCAACTACAACCAAAC |
| HLA-DNA | NM_002119 | GAGGTTAAAGGAAGTTTTGGA | AAACTAAATTCTCCCAATACC |
| HLA-F | NM_018950 | TTGTTGTTTTAGGGGTTTTGG | TCCTTCCCATTCTCCAAATATC |
| MLH1 | NM_000249 | TTTAAGGTAAGAGAATAGGT | TTAACCCTACTCTTATAACC |
| HSPA2 | NM_021979 | AGAGGAGATATTTTTTATGG or AAGGATAATAATTTGTTGGG | AAAAATCCTACAACAACTTC or CTTAAATACAAACTTAATCC |
| IL13 | NM_002188 | TTTTTAGGGTAGGGGTTGT | CCTTATCCCCCATAACCA |
| l-myc | NM_005377 | AGGTTTGGGTTATTGAGTTT | CATTATTTCCTAACTACCTTATATCTC |
| MC2R | NM_000529 | ATATTTGATATGTTGGGTAG | ACCTACTACAAAAAATCATC |

TABLE 1-continued

List of genes and primer oligonucleotides according to Example 2

| Name | Genbank Entry No. (internet address: ttp://www.ncbi.nlm.nih.gov) | Primer 1 | Primer 2 |
|---|---|---|---|
| ME491/CD63 | NM_001780 | TGGGAGATATTTAGGATGTGA | CTCACCTAAACTTCCCAAA |
| MGMT | NM_002412 | TTGTGAGGTATTGGGAGTTAG | ACCCAAACACTCACCAAAT |
| MRP5 | NM_005688 | ATGAGGTGGGAGGATTGTTT | CATCCAAAATTCTAAACTAA |
| N33 | NM_006765 | TGGAGGAGATATTGTTTTGT | TTTTTCAAATCAAAACCCTACT |
| NCL | NM_005381 | AAGTTGTGTTTTAAAAGGGTTA | AAAAACTAAACCTACCCAATAA |
| NEU1 | NM_016215 | AGGAGGAAGGGTTAATAAAGA | ATCTTCCTACTACTATCTCTAAC |
| NF1 | NM_000267 | TTGGGAGAAAGGTTAGTTTT | ATCCAAACTCCCAATATTCC |
| n-myc | NM_005378 | GGAGGAGTATATTTTGGGTTT | ACAAACCCTACTCCTTACCTC |
| OAT | NM_000274 | TGGAGGTGGATTTAGAGGTA | ACCAAAACCCCAAAACAA |
| POMC | NM_000939 | AGTTTTTAAATAATGGGGAAAT | ACTCTTCTTCCCCTCCTTC |
| PGR | NM_000926 | AGTTGAAGTTATAAGGGGTG | AATAAAAACTCTCAAAAACC |
| RD | NM_002904 | AAGAGTGAGAAGTAGAGGGTT | CTACTCTCTAAAACTCCAAAC |
| SOD1 | NM_000454 | AGGGGAAGAAAAGGTAAGTT | CCCACTCTAACCCCAAACCA |
| TGFA | NM_003236 | GGTTTGTTTGGGAGGTAAG | CCCCCTAAAAACACAAAA |
| TGFB1 | NM_000660 | GGGGAGTAATATGGATTTGG | CCTTTACTAAACACCTCCCATA |
| TNF-beta | X02911 | TTTTTGTTTTTGATTGAAATAGTAG | AAAAACCCCAAAATAAACAA |
| TSP | NM_003246 | TGGTATTTTTGAGGTAGATG | CCCTATCTTCCTACACAAAC |
| UBB | NM_018955 | TTAAGTTATTTAGGTGGAGTTTA | ACCAAAATCCTACCAATCAC |
| UNG | NM_003362 | GTTGGGGTGTTTGAGGAA | CCTCTCCCCTCTAATTAAACA |
| VEGF | NM_003376 | TGGGTAATTTTTAGGTTGTGA | CCCCAAAAACAAATCACTC |
| WT1 | NM_000378 | AAAGGGAAATTAAGTGTTGT | TAACTACCCTCAACTTCCC |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07381808B2). An electronic copy of the "Sequence Listing" will also be available from the USPTO upon request and payment of the fee set forth in 37 CFR 1.19(b)(3).

What is claimed is:

1. An isolated nucleic acid consisting of at least 100 contiguous nucleotides of a chemically pretreated genomic DNA sequence from nucleotides 4456-4928 of SEQ ID NO: 37 or the corresponding portion of SEQ ID NO: 38.

2. The nucleic acid of claim 1, wherein the contiguous base sequence comprises at least one CpG dinucleotide.

3. The nucleic acid of claim 2, wherein the cytosine of the CpG dinucleotide is located approximately in the middle third of the contiguous base sequence.

4. A set of oligomers, comprising at least two nucleic acid oligomers according to any one of claims 1 to 3.

5. A set of oligomers according to claim 4, comprising oligomers for detecting the methylation state of all CpG dinucleotides within the genomic region corresponding to nucleotides 4456 through 4928 of SEQ ID NO:37 or the corresponding portion of SEQ ID NO:38.

6. A set of at least two oligomers, according to claim 4, which can be used as primer oligonucleotides for the amplification of nucleotides 4456 through 4928 of SEQ ID NO:37, the corresponding portion of SEQ ID NO:38, or contiguous portions thereof.

7. The set of oligomers of claim 6, wherein at least one oligonucleotide is bound to a solid phase.

8. A method for manufacturing an arrangement of different nucleic acid oligomers, comprising:

obtaining at least one oligomer according to any one of claims 1 to 3; and coupling the at least one oligomer to a carrier material.

9. An arrangement of different oligomers, comprising at least one oligomer according to any one of claims 1 to 3 coupled to a carrier material.

10. The arrangement of claim 9, wherein the oligomers are arranged on a solid phase in the form of a rectangular or hexagonal lattice.

11. The arrangement according to claim 9, wherein the carrier material comprises a solid phase comprising a material selected from the group consisting of silicon, glass, polystyrene, aluminium, steel, iron, copper, nickel, silver, gold, and combinations thereof.

12. A kit, comprising: a bisulfite reagent; and at least one oligomer according to claim 1.

13. The kit of claim 12, further comprising standard methylation assay reagents for performing a methylation assay selected from the group consisting of MS-SNuPE, COBRA, array-based assays, and combinations thereof.

14. A nucleic acid away having utility for analysing prostate cell proliferative disorders, comprising at least one nucleic acid according to any one of claims 1 to 3.

15. The nucleic acid of claim 1, comprising at least one of an oligonucleotide, and a peptide nucleic acid (PNA)-oligomer.

16. The arrangement of claim 9, wherein the at least one oligomer is a peptide nucleic acid (PNA)-oligomer.

* * * * *